United States Patent
Mangel et al.

(10) Patent No.: US 6,759,413 B2
(45) Date of Patent: Jul. 6, 2004

(54) USE OF COX-2 INHIBITORS AS GASTROPROKINETICS

(75) Inventors: Allen Wayne Mangel, Chapel Hill, NC (US); Alan Naylor, Stevenage (GB)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 10/182,080

(22) PCT Filed: Feb. 1, 2001

(86) PCT No.: PCT/GB01/00423
§ 371 (c)(1),
(2), (4) Date: Jul. 25, 2002

(87) PCT Pub. No.: WO01/56573
PCT Pub. Date: Aug. 9, 2001

(65) Prior Publication Data
US 2003/0022897 A1 Jan. 30, 2003

(30) Foreign Application Priority Data
Feb. 1, 2000 (GB) .............................. 0002336

(51) Int. Cl.⁷ .......................................... A61K 31/5025
(52) U.S. Cl. ..................................................... 514/248
(58) Field of Search ................................ 514/248, 275, 514/300, 316, 374, 378, 406, 473, 567, 605

(56) References Cited

U.S. PATENT DOCUMENTS
2001/0041726 A1 * 11/2001 Bandarage et al. ......... 514/361

FOREIGN PATENT DOCUMENTS
| EP | 0 812 541 A | 12/1997 |
| GB | 2 325 161 A | 11/1998 |
| WO | WO 00 48583 A | 8/2000 |

OTHER PUBLICATIONS
Josephs, MD; et al. "Products of Cyclooxygenase–2 Catalysis Regulate Postoperative Bowel Motility." Journal of Surgical Research, vol. 86, No. 1, 1999, p. 52.

Hayakawa, T; et al. "Effects of DAI–Kenchu–TO on Intestinal Obstruction Following Laparotomy." Journal of Smooth Muscle Research, vol. 35, No. 2, 1999, pp. 47–54.

Morgan, G: "Beneficial Effect of NSAIDS in the Gastrointestinal Tract." European Journal of Gastroenterology and Hepatology, vol. 11, No. 4, 1999, pp. 395–400.

* cited by examiner

Primary Examiner—Phyllis G. Spivack
(74) Attorney, Agent, or Firm—Lorie Ann Morgan

(57) ABSTRACT

The invention provides a COX-2 inhibitor or a pharmaceutically acceptable derivative thereof for use in the treatment of a disorder ameliorated by a gastroprokinetic.

4 Claims, 5 Drawing Sheets

INHIBITION OF COX ISOFORMS ENHANCES CHOLINERGIC CONTRACTIONS
(Canine antrum circular muscles)

Fig 3

Fig 4

USE OF COX-2 INHIBITORS AS GASTROPROKINETICS

CROSS-REFERENCES TO RELATED APPLICATIONS

This application is a Rule 371 Application of PCT Application No. GB01/00423, filed 1 Feb. 2001, which claims priority to GB application Ser. No. 0002336.6, filed 1 Feb. 2000.

BACKGROUND OF THE INVENTION

The invention relates to a new medical use for compounds which act as inhibitors of cyclooxygenase-2 (COX-2).

It is only recently that the enzyme COX has been discovered to exist in two isoforms, COX-1 and COX-2. COX-1 corresponds to the originally identified constitutive enzyme while COX-2 is rapidly and readily inducible by a number of agents including mitogens, endotoxin, hormones, cytokines and growth factors. Prostaglandins generated by the action of COX have both physiological and pathological roles. It is generally believed that COX-1 is largely responsible for the important physiological functions such as maintenance of gastrointestinal integrity and renal blood flow. In contrast the inducible form, COX-2, is believed to be largely responsible for the pathological effects of prostaglandins where rapid induction of the enzyme occurs in response to such agents as inflammatory agents, hormones, growth factors and cytokines. A selective inhibitor of COX-2 would therefore have anti-inflammatory, anti-pyretic and analgesic properties, without the potential side effects associated with inhibition of COX-1.

COX-2 inhibitors may be identified by methods well known in the art, for example as described in WO99/12930 (especially pages 25 and 26).

In various animal models, by-products of the COX pathway have been shown to be inhibitory to gastrointestinal motility. Specifically, stimulation in motor activity occurs following administration of non-selective COX inhibitors, such as indomethacin, and inhibition in motor activity follows exogenous administration of some prostaglandins. Additionally, intravenous administration of indomethacin has also been shown to increase lower esophageal sphincter pressure (LESP) in man. The observed changes in motor activity have been attributed to products of the COX-1 pathway, since the trigger for induction of COX-2, the inducible isoform of the COX enzyme, is not readily apparent.

DETAILED DESCRIPTION OF THE INVENTION

Surprisingly, it has now been found that COX-2 inhibitors stimulate gastrointestinal motility and hence act as gastroprokinetics.

Accordingly, COX-2 inhibitors are of use in the treatment of disorders ameliorated by a gastroprokinetic. Disorders ameliorated by gastroprokinetic agents include ileus, for example post-operative ileus and ileus during sepsis; gastroesophageal reflux disease (GORD, or its synonym GERD); gastroparesis, such as diabetic gastroparesis; and other functional bowel disorders, such as non-ulcerative dyspepsia (NUD) and non-cardiac chest pain (NCCP).

According to one aspect, the invention therefore provides a method of treatment of a mammal, including man, suffering from a disorder ameliorated by a gastroprokinetic which comprises administering an effective amount of a COX-2 inhibitor or a pharmaceutically acceptable derivative thereof.

In another aspect, the invention provides the use of a COX-2 inhibitor or a pharmaceutically acceptable derivative thereof in the manufacture of a medicament for the treatment of a disorder ameliorated by a gastroprokinetic.

By pharmaceutically acceptable derivative is meant any pharmaceutically acceptable salt or solvate of a COX-2 inhibitor or any other compound, which upon administration to the recipient is capable of providing (directly or indirectly) a COX-2 inhibitor or an active metabolite or residue thereof.

A number of COX-2 inhibitors have been disclosed, for example those mentioned in the following patent applications:

AU9719132, CA2164559, CA2180624, EP-799823, EP-846689, EP-863134, FR2751966, GB2283745, GB2319772, GB2320715, JP08157361, U.S. Pat. Nos. 5,510,368, 5,681,842, 5,686,460, 5,776,967, 5,783,597, 5,824,699, 5,830,911, 5,859,036, 5,869,524, WO94/13635, WO94/20480, WO94/26731, WO95/00501, WO95/21817, WO96/03385, WO96/03387, WO96/06840, WO96/09293, WO96/09304, WO96/13483, WO96/16934, WO96/19462, WO96/19463, WO96/19469, WO96/21667, WO96/23786, WO96/24584, WO96124585, WO96/25405, WO96/26921, WO96/31509, WO96/36617, WO96/36623, WO96/37467, WO96/37469, WO96/38418, WO96/38442, WO96/40143, WO97103953, WO97/09977, WO97/13755, WO97/13767, WO97/14691, WO97/16435, WO97/25045, WO97/25046, WO97125047, WO97/25048, WO97/27181, WO97/28120, WO97/28121, WO97/30030, WO97/34882, WO97/36863, WO97/37984, WO97/38986, WO97/40012, WO97/46524, WO97/46532, WO98/03484, WO98/04527, WO98/06708, WO98/06715, WO98/07425, WO98/11080, WO98/15528, WO98/21195, WO98122442, WO98/28292, WO98/29382, WO98/41511, WO98/41516, WO98/43966, WO98/45294, WO98/46594, WO98/46611, WO98/47890, WO98/51667, WO98/57924, WO99/01455, WO99/05104, WO99/10331, WO99/10332, WO99/11605, WO99/12930, WO99/14194, WO99/14195, WO99/14205, WO99/15505, ZA9704806 and ZA9802828;

as well as those mentioned in the following patent applications:

EP-921119, EP-937722, EP-985666, EP-1065204 DE19845446 U.S. Pat. Nos. 5,916,891, 6,083,969, JP11302266, JP2000136182, WO99/18093, WO99/23087, WO99/24404, WO99/25695, WO99/32448, WO99/33796, WO99/35130, WO99/37600, WO99/41224, WO99/43664, WO99/51559, WO99/58523, WO99/61436, WO99/62884, WO99/63939, WO99/64415, WO00/06576, WO00/08024, WO00/10563, WO00/10993, WO00/14082, WO00/17175, WO00/18753, WO00/20371, WO00/20398, WO00/23426, WO00/23433, WO00/26216, WO00/31063, WO00/32567, WO00/39116, WO00/40087, WO00/40243, WO00/50425, WO00/52008, WO00/55139, WO00/61571, WO00/66562 and PCT.EP00.11673 (unpublished at the filing date of the instant application);

all incorporated herein by reference (and hereinafter collectively referred to as the compounds of Group A). The above applications also describe, in relation to the COX-2 inhibitors they disclose, both suitable methods for their preparation and formulation, and doses for their administration.

In another aspect, the invention provides a method of treatment of a mammal, including man, suffering from a disorder ameliorated by a gastroprokinetic which comprises administering an effective amount of a compound of Group A or a pharmaceutically acceptable derivative thereof.

In another aspect, the invention provides the use of a compound of Group A or a pharmaceutically acceptable derivative thereof in the manufacture of a medicament for the treatment of a disorder ameliorated by a gastroprokinetic.

In the abovementioned WO99/12930 there is disclosed 2-(4-ethoxy-phenyl)-3-(4-methanesulfonyl-phenyl)-pyrazolo[1,5-b]pyridazine, which may be represented by formula (I)

(I)

and pharmaceutically acceptable derivatives thereof.

In the abovementioned WO96/31509 there is disclosed 8-acetyl-3-(4-fluoro-phenyl)-2-(4-methanesulfonyl-phenyl)-imidazo[1,2-a]pyridine, which may be represented by formula (II)

(II)

and pharmaceutically acceptable derivatives thereof.

In the abovementioned WO00/26216 there is disclosed 4-[2-(3-fluoro-phenyl)-6-trifluoromethyl-pyrazolo[1,5-a]pyridin-3-yl]-benzenesulfonamide, which may be represented by formula (III)

(III)

and pharmaceutically acceptable derivatives thereof.

In the abovementioned PCT.EP00.11673 there is disclosed N-isobutyl-4-[4-(methylsulfonyl)phenyl]-6-(trifluoromethyl)pyrimidin-2-amine, which may be represented by formula (IV)

(IV)

and pharmaceutically acceptable derivatives thereof.

Further examples of compounds from within Group A include celecoxib, rofecoxib, valdecoxib and parecoxib; and pharmaceutically acceptable derivatives thereof.

Still further examples of compounds from within Group A include: etoricoxib (MK663); 4-(4-cyclohexyl-2-methyl-5-oxazolyl)-2-fluorobenzenesulfonamide (JTE-522); nimesulide; flosulide; 5,5-dimethyl-4-(4-methylsulfonylphenyl)-3-(2-propoxy)-5H-furanone, DFP; methanesulfonamide, N-(2-(cyclohexyloxy)-4-nitrophenyl) (NS398); and 5-methanesulfonamido-6-(2,4-difluorothiophenyl)-1-indanone (L-745337); and pharmaceutically acceptable derivatives thereof.

A further example of a compound from within Group A is COX 189.

It will be appreciated by the skilled person that, as a consequence of the use of different chemical naming conventions (e.g. IUPAC, CA and so on), the same compound may be referred to by different chemical names.

In another aspect, the invention provides a method of treatment of a mammal, including man, suffering from a disorder ameliorated by a gastroprokinetic which comprises administering an effective amount of: 2-(4-ethoxy-phenyl)-3-(4-methanesulfonyl-phenyl)-pyrazolo[1,5-b]pyridazine; 8-acetyl-3-(4-fluoro-phenyl)-2-(4-methanesulfonyl-phenyl)-imidazo[1,2-a]pyridine; 4-[2-(3-fluoro-phenyl)-6-trifluoromethyl-pyrazolo[1,5-a]pyridin-3-yl]-benzenesulfonamide; N-isobutyl-4-[4-(methylsulfonyl)phenyl]-6-(trifluoromethyl)pyrimidin-2-amine; celecoxib; rofecoxib; valdecoxib; parecoxib; COX 189; etoricoxib (MK663); 4-(4-cyclohexyl-2-methyl-5-oxazolyl)-2-fluorobenzenesulfonamide (JTE-522); nimesulide; flosulide; 5,5-dimethyl-4-(4-methylsulfonylphenyl)-3-(2-propoxy)-5H-furanone (DFP); methanesulfonamide, N-(2-(cyclohexyloxy)-4-nitrophenyl) (NS398); or 5-methanesulfonamido-6-(2,4-difluorothiophenyl)-1-indanone (L-745337) (and hereinafter collectively referred to as the compounds of Group B); or a pharmaceutically acceptable derivative thereof.

In another aspect, the invention provides the use of a compound of Group B or a pharmaceutically acceptable derivative thereof in the manufacture of a medicament for the treatment of a disorder ameliorated by a gastroprokinetic.

In another aspect, the invention provides a method of treatment of a mammal, including man, suffering from a disorder ameliorated by a gastroprokinetic which comprises administering an effective amount of 2-(4-ethoxy-phenyl)-3-(4-methanesulfonyl-phenyl)-pyrazolo[1,5-b]pyridazine or a pharmaceutically acceptable derivative thereof.

In another aspect, the invention provides the use of 2-(4-ethoxy-phenyl)-3-(4-methanesulfonyl-phenyl)-pyrazolo[1,5-b]pyridazine or a pharmaceutically acceptable derivative thereof in the manufacture of a medicament for the treatment of a disorder ameliorated by a gastroprokinetic.

Suitable pharmaceutically acceptable salts of 2-(4-ethoxy-phenyl)-3-(4-methanesulfonyl-phenyl)-pyrazolo[1,5-b]pyridazine include acid addition salts formed with inorganic or organic acids (for example hydrochlorides, hydrobromides, sulphates, phosphates, benzoates, naphthoates, hydroxynaphthoates, p-toluenesulphonates, methanesulphonates, sulphamates, ascorbates, tartrates, salicylates, succinates, lactates, glutarates, glutaconates, acetates, tricarballylates, citrates, fumarates and maleates), and solvates (for example hydrates) thereof.

Preferably, 2-(4-ethoxy-phenyl)-3-(4-methanesulfonyl-phenyl)-pyrazolo[1,5-b]pyridazine is employed in the form of its free base.

The invention includes all isomers of 2-(4-ethoxy-phenyl)-3-(4-methanesulfonyl-phenyl)-pyrazolo[1,5-b]pyridazine and its pharmaceutically acceptable derivatives, including all tautomeric and optical forms, and mixtures thereof, including racemic mixtures.

In another aspect the invention provides a COX-2 inhibitor or a pharmaceutically acceptable derivative thereof for use in the treatment of a disorder ameliorated by a gastroprokinetic.

In another aspect the invention provides a compound of Group A or a pharmaceutically acceptable derivative thereof for use in the treatment of a disorder ameliorated by a gastroprokinetic.

In another aspect the invention provides a compound of Group B or a pharmaceutically acceptable derivative thereof for use in the treatment of a disorder ameliorated by a gastroprokinetic.

In another aspect the invention provides celecoxib, rofecoxib, valdecoxib or parecoxib; or a pharmaceutically acceptable derivative thereof, for use in the treatment of a disorder ameliorated by a gastroprokinetic.

In another aspect the invention provides 2-(4-ethoxy-phenyl)-3-(4-methanesulfonyl-phenyl)-pyrazolo[1,5-b]pyridazine or a pharmaceutically acceptable derivative thereof for use in the treatment of a disorder ameliorated by a gastroprokinetic.

In another aspect the invention provides a COX-2 inhibitor or a pharmaceutically acceptable derivative thereof for use in the treatment of GORD.

In another aspect the invention provides a COX-2 inhibitor or a pharmaceutically acceptable derivative thereof for use in the treatment of ileus.

In another aspect the invention provides a COX-2 inhibitor or a pharmaceutically acceptable derivative thereof for use in the treatment of gastroparesis, such as diabetic gastroparesis.

In another aspect the invention provides a COX-2 inhibitor or a pharmaceutically acceptable derivative thereof for use in the treatment of NUD.

In another aspect the invention provides a COX-2 inhibitor or a pharmaceutically acceptable derivative thereof for use in the treatment of NCCP.

Within the above aspects of the invention, the use of a COX-2 inhibitor of Group A; such as a COX-2 inhibitor of Group B; for example celecoxib, rofecoxib, valdecoxib or parecoxib; in particular 2-(4-ethoxy-phenyl)-3-(4-methanesulfonyl-phenyl)-pyrazolo[1,5-b]pyridazine; is preferred.

It is to be understood that reference to treatment includes both treatment of established symptoms and prophylactic treatment, unless explicitly stated otherwise.

It will be appreciated by the skilled person that it may be advantageous to administer one (or more) other therapeutic agent(s) in combination with a COX-2 inhibitor for the treatment of gastroprokinetic ameliorated conditions. Examples of suitable therapeutic agents for adjunctive therapy include gastroprokinetic agents, such as cinitapride, cisapride, mosapride, itopride, prucalopride, idremcinal, lirexapride or metocloperamide; proton pump inhibitors, such as omeprazole, pantoprazole, rabeprazole, polaprezinc, lansoprazole, leminoprazole, esomeprazole and tenatoprazole; reversible proton pump antagonists, such as AR-H047108 and YH-1885; 5-$HT_3$ antagonists, such as alosetron; 5-$HT_4$ agonists, such as tegaserod; 5-$HT_4$ antagonists, such as piboserod; and $H_2$ antagonists, such as cimetidine, ebrotidine, famotidine, ranitidine, roxatidine, nizatidine, lafutidine, pibutine and osutidine; or pharmaceutically acceptable derivatives thereof.

In view of their surprising gastroprokinetic activity, COX-2 inhibitors may also be administered with one (or more) other therapeutic agent(s) to enhance the amount and rate of absorption of the other therapeutic agent(s). Examples of suitable therapeutic agents for such adjunctive therapy include 5-$HT_1$ receptor agonists, such as triptans (e.g. sumatriptan and naratriptan).

Thus in another aspect the invention provides the use, as a gastroprokinetic, of a COX-2 inhibitor, or a pharmaceutically acceptable derivative thereof, to enhance the amount of absorption of an orally administered $5HT_1$ receptor agonist, or a pharmaceutically acceptable derivative thereof.

In another aspect the invention provides the use as a gastroprokinetic of a COX-2 inhibitor, or a pharmaceutically acceptable derivative thereof, to enhance the rate of absorption of an orally administered $5HT_1$ receptor agonist, or a pharmaceutically acceptable derivative thereof.

It will be appreciated that adjunctive therapy may take the form of simultaneous or sequential coadministration of therapeutic agents and, when administration is sequential, either the COX-2 inhibitor or the other therapeutic agent (or one of the other therapeutic agents) may be administered first.

Conveniently, a COX-2 inhibitor or a pharmaceutically acceptable derivative thereof may be formulated in conventional manner using one or more pharmaceutically acceptable carriers or excipients. Thus a COX-2 inhibitor or a pharmaceutically acceptable derivative thereof may, for example, be formulated for oral, sub-lingual, buccal, parenteral, rectal or intranasal administration, or in a form suitable for administration by inhalation or insufflation (either through the mouth or nose), or in a form suitable for topical administration.

For oral administration the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrates (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid).

For buccal administration the compositions may take the form of tablets or lozenges formulated in conventional manner.

A COX-2 inhibitor or a pharmaceutically acceptable derivative thereof may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multi-dose containers, optionally with an added preservative.

The compositions for parenteral administration may take such forms as suspensions, solutions or emulsions in oily or aqueous vehicles, and may contain formulatory agents such as suspending, stabilising and/or dispersing agents. Alternatively, the compositions may be in dry form such as a powder, crystalline or freeze-dried solid for constitution with a suitable vehicle, e.g. sterile pyrogen-free water or isotonic saline before use. They may be presented, for example, in sterile ampoules or vials.

A COX-2 inhibitor or a pharmaceutically acceptable derivative thereof may also be formulated in rectal compositions such as suppositories or retention enemas.

Tablets for sub-lingual administration may be formulated in a conventional manner.

For intranasal administration, or administration by inhalation or insufflation, a COX-2 inhibitor or a pharmaceutically acceptable derivative thereof may be formulated in a conventional manner.

For topical administration the pharmaceutical compositions may be liquids, for example solutions, suspensions or emulsions presented in the form of creams or gels.

In addition to the formulations described previously, a COX-2 inhibitor or a pharmaceutically acceptable derivative thereof may also be formulated as a depot preparation. Such long acting formulations may be administered by implantation (for example subcutaneously, transcutaneously or intramuscularly) or by intramuscular injection. Thus, for example, the compositions may be formulated with suitable polymeric or hydrophobic materials (for example as an emulsion in an acceptable oil) or ion exchange resins, or as sparingly soluble derivatives, for example, as a sparingly soluble salt.

It will be appreciated that the precise therapeutic dose of a COX-2 inhibitor, expressed in the form of its free base, will depend on the age and condition of the patient and the nature of the disorder to be treated and will be at the ultimate discretion of the attendant physician.

However, in general, effective doses for the treatment of a disorder in man will lie in the range of 0.001 to 1000 mg, such as 0.01 to 500 mg, preferably 0.05 to 250 mg, for example 0.5 to 100 mg per unit dose, which could be administered in single or divided doses, for example, 1 to 4 times per day.

In a preferred embodiment, effective doses of 2-(4-ethoxy-phenyl)-3-(4-methanesulfonyl-phenyl)-pyrazolo[1,5-b]pyridazine for the treatment of a disorder in man will lie in the range of 0.1 to 1000 mg, such as 1 to 500 mg, preferably 10 to 250 mg, for example 25, 50 or 100 mg of 2-(4-ethoxy-phenyl)-3-(4-methanesulfonyl-phenyl)-pyrazolo[1,5-b]pyridazine per unit dose, which could be administered in single or divided doses, for example, 1 to 4 times per day.

The data that follows illustrates and supports the invention, but does not limit the invention in any way. Indomethacin is a non-selective COX inhibitor. Celecoxib, 8-acetyl-3-(4-fluoro-phenyl)-2-(4-methanesulfonyl-phenyl)-imidazo[1,2-a]pyridine and 2-(4-ethoxy-phenyl)-3-(4-methanesulfonyl-phenyl)-pyrazolo[1,5-b]pyridazine are selective COX-2 inhibitors. Cisapride is a gastroprokinetic agent.

Smooth Muscle in vitro Model of Gastric Propulsion

Agents which stimulate antral smooth muscle activity would be expected to enhance the rate of gastric emptying by propulsion of contents in the aboral direction. By contrast, fundic relaxation could lead to delayed emptying of the stomach as the upper stomach would serve as a reservoir for gastric contents.

The effects of test agents were evaluated on strips of canine antrum circular muscles (n=4–8 strips) suspended in organ baths bathed with Krebs solution. Following establishment of baseline tension, acetylcholine ("ACh"; 1 $\mu$M), indomethacin (10 $\mu$M), or 8-acetyl-3-(4-fluoro-phenyl)-2-(4-methanesulfonyl-phenyl)-imidazo[1,2-a]pyridine ("8-Acetyl- . . . "; 10 $\mu$M) were applied and tension changes monitored and recorded on a polygraph.

Figure 1:
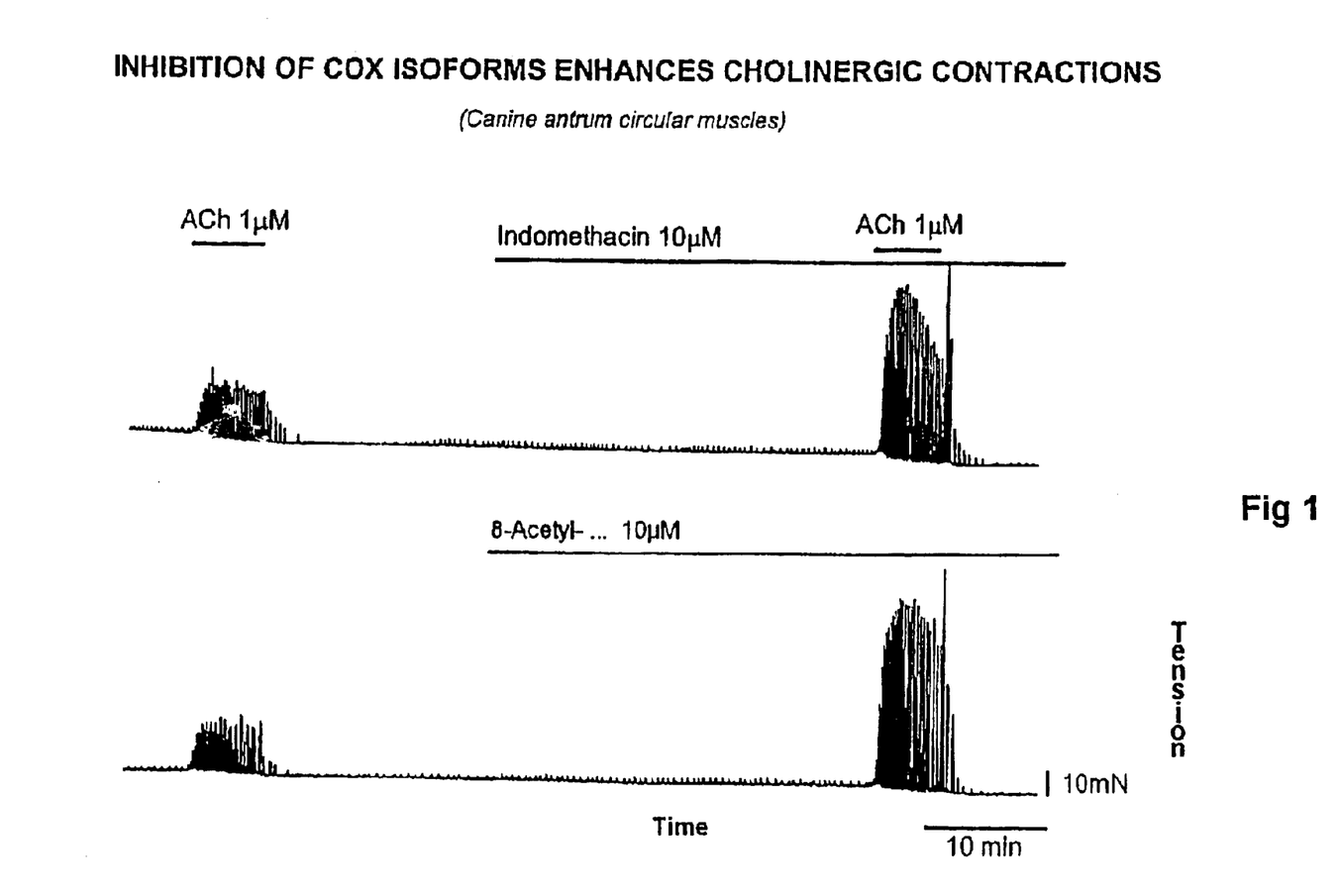

The nonselective COX inhibitor, indomethacin, was observed to sensitise antral circular muscle segments to the addition of acetylcholine, such that enhanced acetylcholine-induced contractions were noted following treatment with indomethacin. The effects of the selective COX-2 inhibitor 8-acetyl-3-(4-fluoro-phenyl)-2-(4-methanesulfonyl-phenyl)-imidazo[1,2-a]pyridine were also evaluated on antral mechanical activity and produced a similar degree of sensitisation for acetylcholine-induced contractility as seen with indomethacin (FIG. 1).

Figure 2:
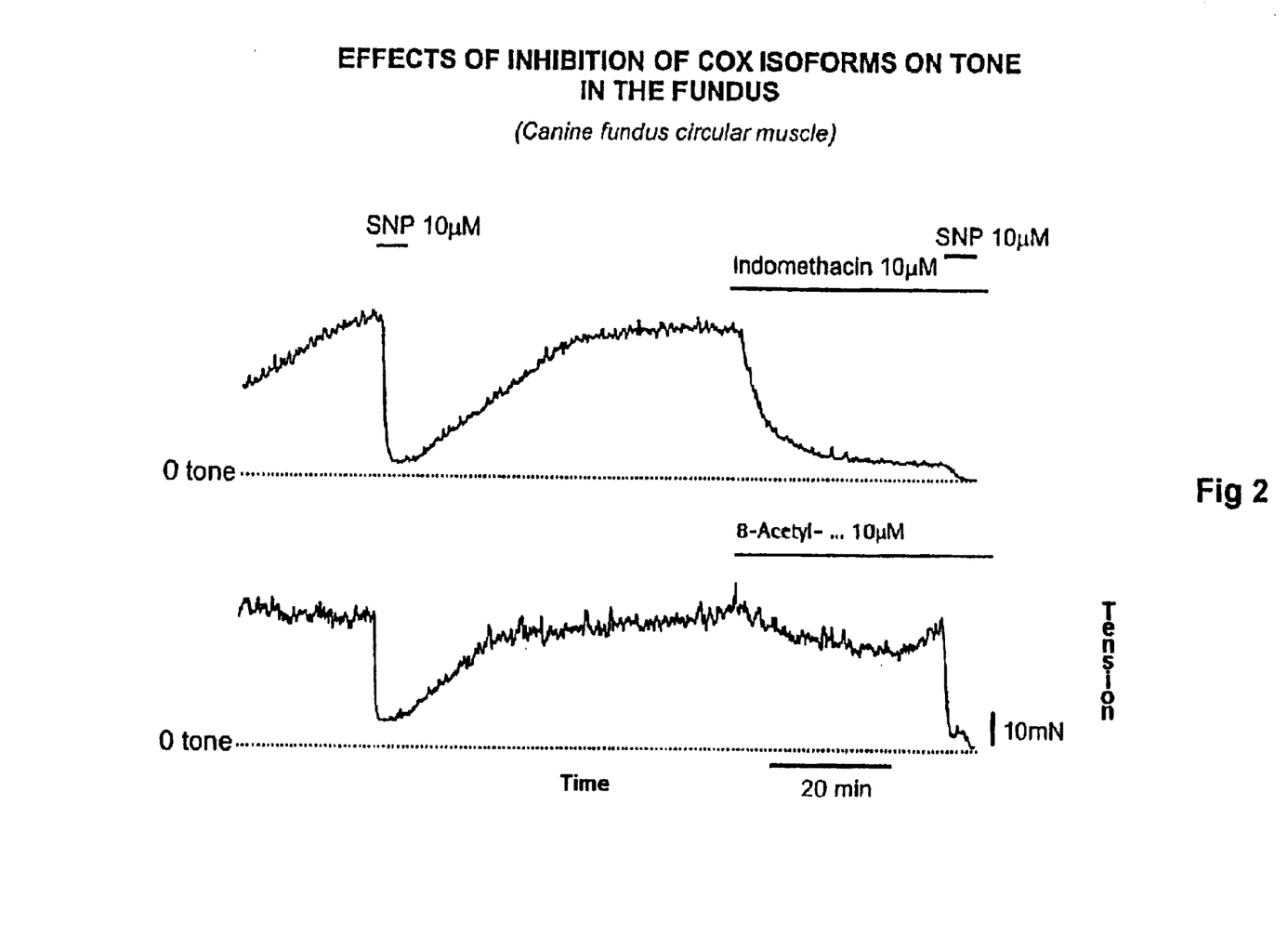

By contrast to the above results, strips of canine fundic circular muscle (n=6–8) showed a complete relaxation following treatment with sodium nitroprusside (SNP, 10 $\mu$M) and a near complete relaxation following indomethacin (10 $\mu$M). 8-Acetyl-3-(4-fluoro-phenyl)-2-(4-methanesulfonyl-phenyl)-imidazo[1,2-a]pyridine (10 $\mu$M), on the other hand, produced only small changes in tension (FIG. 2).

The motility consequences of such differences appear to represent the explanation for the enhancement of gastric emptying by selective COX-2 inhibitors, but not indomethacin. Differences seen with indomethacin and 8-acetyl-3-(4-fluoro-phenyl)-2-(4-methanesulfonyl-phenyl)-imidazo[1,2-a]pyridine appear to represent a consequence of inhibition of synthesis of COX-1 mediated products by indomethacin which would not be seen with the selective COX-2 inhibitor.

Figure 5:
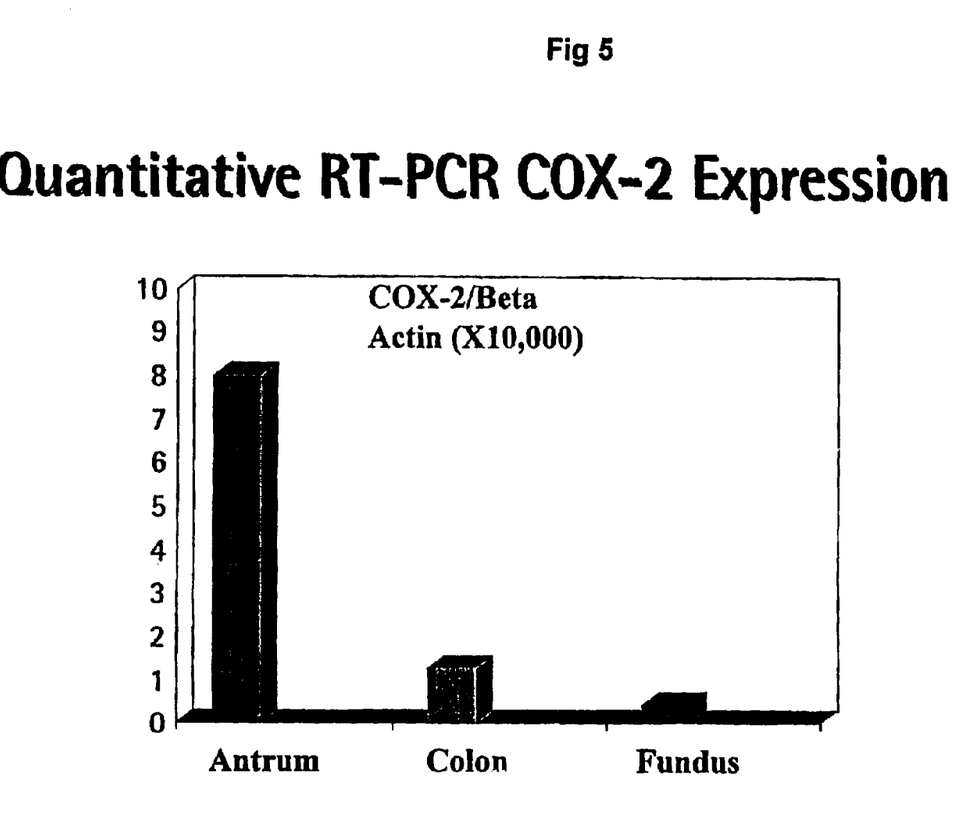

Changes in mechanical activity following administration of 8-acetyl-3-(4-fluoro-phenyl)-2-(4-methanesulfonyl-phenyl)-imidazo[1,2-a]pyridine are suggestive of constitutive expression of COX-2. Constitutive production of COX-2 mRNA in dog antral, duodenal and colonic smooth muscle was confirmed by polymerase chain reaction (PCR) and provides strong support for the utility of COX-2 inhibitors as gastroprokinetics (FIG. 5).

Activity In Vivo: Dog Model of Gastric Emptying

Beagle dogs were treated for three days with test agents (po administration): placebo BID; cisapride 0.14 mg/kg TID; celecoxib 2.8 mg/kg BID; or 8-acetyl-3-(4-fluoro-phenyl)-2-(4-methanesulfonyl-phenyl)-imidazo[1,2-a]pyridine 1.2 mg/kg BID. Solid phase gastric emptying was measured on the fourth day following am dosing. The same three animals were used for evaluation of each agent, thus reducing any interanimal variations.

Isotope-labeled solid food was fed to the dogs for their morning meal and animals were then placed under a gamma camera and scans performed over the 24 to 36 hours.

Figure 3:
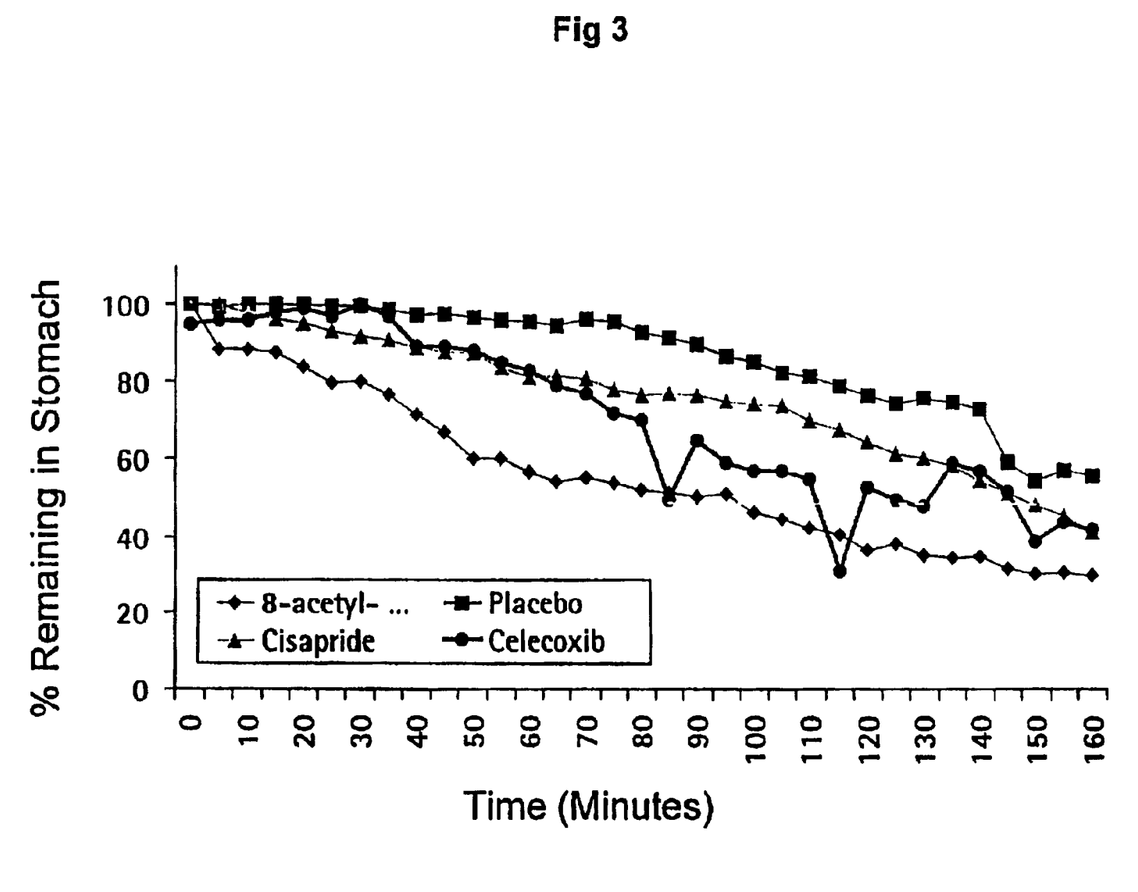

Cisapride, celecoxib and 8-acetyl-3-(4-fluoro-phenyl)-2-(4-methanesulfonyl-phenyl)-imidazo[1,2-a]pyridine all increased the rate of gastric emptying (FIG. 3). Thus, treatment with COX-2 inhibitors enhances the rate of gastric emptying and hence COX-2 inhibitors serve as gastroprokinetic agents.

Activity In Vivo: Dog Model of Lower Esophageal Sphincter Pressure (LESP)

Six adult dogs were instrumented with 14 French esophagostomy tubes. Animals were treated for 3 days with placebo (BID), cisapride (0.14 mg/kg TID) or celecoxib (1.2 mg/kg BID). On day 4 dogs received their am dose of test agent and water perfused manometry catheters were inserted through the esophagostomy tubes. Lower esophageal sphincter pressures (LESPs) were then monitored.

Figure 4:
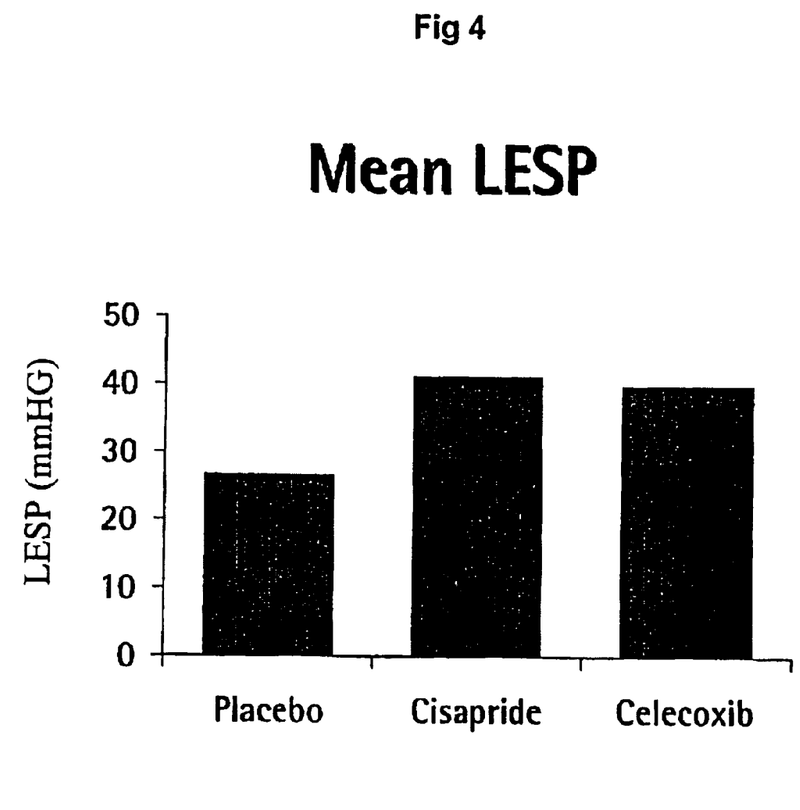

Cisapride increased LESP as compared to placebo treated animals. Celecoxib was noted to increase LESP to a similar degree as cisapride (FIG. 4).

Thus, in addition to speeding gastric emptying, COX-2 inhibitors display a second characteristic of gastroprokinetic agents, that of increasing LESP. Increasing LESP would be of therapeutic benefit in preventing reflux of materials from the stomach to the esophagus.

Activity In Vivo: Rat Model of Post Operative Ileus

The selective COX-2 inhibitor 2-(4-ethoxy-phenyl)-3-(4-methanesulfonyl-phenyl)-pyrazolo[1,5-b]pyridazine was evaluated in a rat model of post-operative ileus. The methodology represents a modification of the procedure described by McGill et al, Gastroenterology 116: A1040 (1999).

Rats (fourteen) received 0.5 cc of skimmed milk with methylene blue by gavage. Either vehicle (six rats) or 2-(4-ethoxy-phenyl)-3-(4-methanesulfonyl-phenyl)-pyrazolo[1,5-b]pyridazine (eight rats) was then administered by intravenous infusion. Rats were sacrificed four hours post-gavage and the distance the methylene blue meal traversed the intestine measured. The pylorus was set at 0 cm. With vehicle treatment, the meal traversed $49.3 \pm 1.3$ cm while with 2-(4-ethoxy-phenyl)-3-(4-methanesulfonyl-phenyl)-pyrazolo[1,5-b]pyridazine (3 mg/kg), the meal traversed $67.8 \pm 1.1$ cm ($p<0.05$).

Thus the selective COX-2 inhibitor 2-(4-ethoxy-phenyl)-3-(4-methanesulfonyl-phenyl)-pyrazolo[1,5-b]pyridazine produced a significant stimulation in gastrointestinal transit.

What is claimed is:

1. A method of treatment of a mammal suffering from NUD which comprises administering an effective amount of 2-(4-ethoxy-phenyl)-3-(4-methanesulfonyl-phenyl)-pyrazolo[1,5-b]pyridazine or a pharmaceutically acceptable derivative.

2. A method of treatment according to claim 1 wherein 2-(4-ethoxy-phenyl)-3-(4-methanesulfonyl-phenyl)-pyrazolo[1,5-b]pyridazine is in the form of its free base.

3. A method of treatment of man suffering from NUD which comprises administering an effective amount of 2-(4-ethoxy-phenyl)-3-(4-methanesulfonyl-phenyl)-pyrazolo[1,5-b]pyridazine or a pharmaceutically acceptable derivative.

4. A method of treatment according to claim 3 wherein 2-(4-ethoxy-phenyl)-3-(4-methanesulfonyl-phenyl)-pyrazolo[1,5-b]pyridazine is in the form of its free base.

* * * * *